United States Patent
Shieh et al.

(10) Patent No.: US 10,468,124 B2
(45) Date of Patent: Nov. 5, 2019

(54) PROCESS FOR DESIGNING AND PRODUCING COOLING FLUIDS

(75) Inventors: Tenghua Tom Shieh, Ann Arbor, MI (US); Shohei Nomura, Ann Arbor, MI (US); Erich Benjamin Fiederlein, Ann Arbor, MI (US); Kiyotaka Yamashita, Ann Arbor, MI (US)

(73) Assignee: Toyota Motor Engineering & Manufacturing North America, Inc., Plano, TX (US)

( * ) Notice: Subject to any disclaimer, the term of this patent is extended or adjusted under 35 U.S.C. 154(b) by 1537 days.

(21) Appl. No.: 13/355,651

(22) Filed: Jan. 23, 2012

(65) Prior Publication Data

US 2013/0187079 A1    Jul. 25, 2013

(51) Int. Cl.
| | |
|---|---|
| *C09K 5/10* | (2006.01) |
| *G16C 20/50* | (2019.01) |
| *B82Y 30/00* | (2011.01) |
| *G16C 10/00* | (2019.01) |
| *G16C 20/30* | (2019.01) |

(52) U.S. Cl.
CPC .............. *G16C 20/50* (2019.02); *B82Y 30/00* (2013.01); *C09K 5/10* (2013.01); *G16C 10/00* (2019.02); *G16C 20/30* (2019.02)

(58) Field of Classification Search
CPC ....................................................... C09K 5/00

USPC ........................................ 252/70, 71; 703/12
See application file for complete search history.

(56) References Cited

U.S. PATENT DOCUMENTS

| | | | |
|---|---|---|---|
| 7,960,167 B2 | 6/2011 | Aizenberg et al. | |
| 2006/0259285 A1 | 11/2006 | Babel et al. | |
| 2007/0043545 A1 | 2/2007 | Yonezawa et al. | |
| 2007/0265805 A1 | 11/2007 | Lee et al. | |
| 2009/0008062 A1 | 1/2009 | Hammel et al. | |
| 2010/0030534 A1* | 2/2010 | Reich et al. | 703/2 |

OTHER PUBLICATIONS

Keblinski et al. "Mechanisms of heat flow in suspensions of nano-sized particles (nanofluids)", International Journal of Heat and Mass Transfer, 45 (2002), 855-863.*

Keblinski et al. "Nanofluids for thermal transport", Materials Today, Jun. 2005, 36-44.*

* cited by examiner

*Primary Examiner* — Jane L Stanley
(74) *Attorney, Agent, or Firm* — Dinsmore & Shohl LLP (57) ABSTRACT

The present invention provides a process for designing and producing a cooling fluid for use in a cooling system. The process uses molecular dynamics to calculate the thermal properties of one or more fluid-nanoparticle solutions, and thereby aids in the study, selection and/or production of desired cooling fluids based on first principle simulations.

7 Claims, 6 Drawing Sheets

PROCESS FOR DESIGNING AND PRODUCING COOLING FLUIDS

BACKGROUND OF THE INVENTION

The use of cooling systems to increase the efficiency of machines such as internal combustion engines is known. Such cooling systems typically include a cooling fluid that travels from a heat source where the cooling fluid conducts or takes heat away from the heat source to a heat sink where the heat is released. In most instances, the cooling system is a closed system such that the cooling fluid recirculates from the heat sink back to the heat source.

Various types of coolants are known to those skilled in the art, for example water, mineral oils, silicon oils, fluorocarbon oils, transformer oils, and the like. In addition, recent research has shown that nanofluids which include a carrier liquid, such as water, dispersed with nanoscale particles may provide improved heat transfer properties. However, given the large number of possible carrier fluids and/or nanoparticles, choosing a fluid-nanoparticle combination suitable for production can be time consuming and costly. Therefore, a process for guiding a researcher, company, etc. in selecting appropriate carrier fluid-nanoparticle combinations for further development and/or production would be desirable.

SUMMARY OF THE INVENTION

The present invention provides a process for designing and/or producing a cooling fluid for use in a cooling system. The process includes selecting a plurality of fluid-particle combinations to be investigated, each of the fluid-particle combinations including a fluid and a plurality of particles. Thereafter, an agglomerate shape distribution for the plurality of particles within the fluid for each of the fluid-particle combinations is calculated. In some instances, a clustering behavior of the plurality of particles within the fluid can be calculated in order to assist in calculating the agglomerate shape distribution.

A thermal conductivity for a resultant agglomerate shape distribution for the plurality of particles within each fluid-particle combination can be calculated. In addition, calculation of an overall thermal conductivity, heat capacity, and the like for each of the fluid-particle combinations can be calculated.

Based on the overall thermal conductivity, heat capacity, etc. for each of the fluid-particle combinations, at least one of the combinations is selected for production and/or further study. If selected for production, a fluid and a plurality of particles corresponding to the at least one selected combination is provided and then mixed to provide a fluid-particle solution for testing and/or use within a cooling system.

In some instances, calculations on one or more of the fluid-particle combinations can be extrapolated to fluid-nanoparticle combinations to provide a fluid-nanoparticle solution for testing and/or use within a cooling system. In other instances, the plurality of particles is a plurality of nanoparticles, e.g. a plurality of nanotubes, and the calculations are performed on a plurality of fluid-nanoparticle combinations. In addition, the calculated agglomerate shape distribution can be a function of at least one fluid-nanotube combination property, for example and for illustrative purposes only, a function of a temperature of the fluid, an aspect ratio of the nanotubes, a length of the nanotubes, a diameter of the nanotubes, a chirality of the nanotubes, a homo-molecular versus hetero-molecular nanotube system, and combinations thereof. The agglomerate shape distribution and/or the thermal conductivity of the agglomerate shape distribution can be calculated using molecular dynamics and the thermal conductivity, heat capacity, etc. of a particular fluid-nanoparticle combination can be calculated using a large-scale molecular dynamics simulator. The calculated thermal conductivity, heat capacity, etc. of a particular fluid-nanoparticle combination can also be a function of at least one fluid-nanotube combination property, for example and for illustrative purposes only, a concentration of the nanotubes within the fluid.

DETAILED DESCRIPTION OF THE PRESENT INVENTION

The present invention provides a process for calculating the thermal properties of a fluid-particle and/or fluid-nanoparticle system based on first principles. As such, the process has a use for cost effectively developing a fluid-particle cooling fluid.

The process includes selecting a plurality of fluid-particle combinations to be studied in order to determine which combination(s) should be produced and/or studied in greater detail. The plurality of fluid-particle combinations can be a plurality of fluid-nanoparticle combinations, however this is not required. After the plurality of fluid-particle combinations has been selected, an agglomeration shape distribution for the particles of each fluid-particle combination is calculated using molecular dynamics. The calculation can include any number of physical, chemical and/or thermal parameters/properties of the fluid and/or nanoparticles, e.g. the concentration of the particles within the fluid, the shape of the particles, the aspect ratio of the particles, the chirality of the particles, the composition of the fluid and/or particles, the temperature of the fluid, and the like. In some instances, a clustering behavior of the particles can be calculated using molecular dynamics in order to aid in determining the agglomerate shape distribution thereof.

After the agglomeration shape distribution for a particular fluid-particle combination has been determined, the thermal conductivity of the agglomerate shape can be calculated, for example through the use of a molecular dynamics simulation. In addition, large scale molecular dynamic simulations can calculate the thermal conductivity, heat capacity, viscosity, and the like of the fluid-particle combination.

After the thermal conductivity, heat capacity, viscosity, and the like have been calculated for at least a subset of the selected fluid-particle combinations, the results can be analyzed in order to determine which of the fluid-particle properties play a significant role in determining the thermal properties of one or more fluid-particle combinations. Such an analysis can be used to focus study on one or more parameters/properties of the fluid and/or particles and/or select or specialize production methods in view of the one or more parameters/properties. In addition, the results can be analyzed to determine which of the fluid-particle combinations should be studied in greater detail and/or produced. In the event that a fluid-particle solution is produced, it can then be tested and/or used within an actual cooling system.

In some instances, one or more of the calculated thermal conductivity, heat capacity, viscosity, etc. properties can be extrapolated to one or more fluid-nanoparticle combinations in order to determine which of one or more fluid-nanoparticle combinations should be studied in greater detail, produced, tested and/or used within an actual cooling system. In other instances, the calculated thermal conductivity, heat capacity, viscosity, etc. properties can be performed on one or more fluid-nanoparticle combinations themselves.

It should be appreciated that the process can thus provide a cooling fluid designed for a particular cooling system. It should also be appreciated that a cooling system can be designed to take advantage of the thermal properties for a particular fluid-particle and/or fluid-nanoparticle solution.

Figure 1:
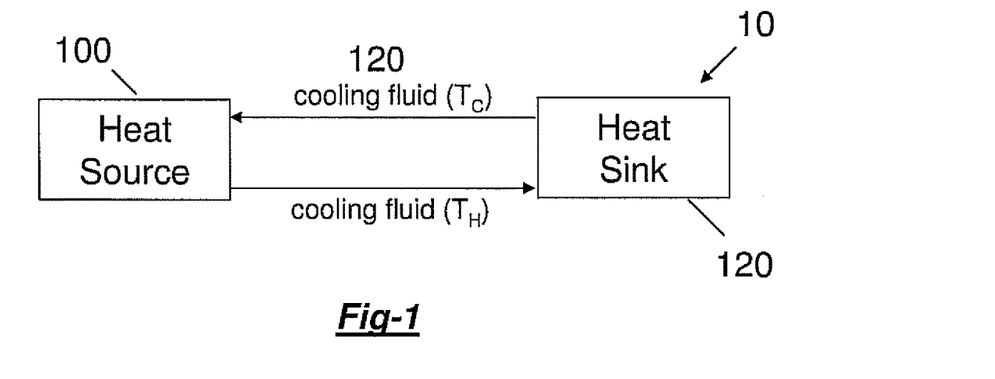
FIG. 1 is a schematic illustration of a cooling system.

Turning now to FIG. 1, a schematic illustration of a cooling system is shown generally at reference numeral 10. The cooling system 10 has a heat source 100 and a heat sink 110. Circulating through and between the heat source 100 and the heat sink 110 is a cooling fluid 120. It is appreciated that the cooling fluid leaving the heat source can have a relatively high temperature compared to the cooling fluid leaving the heat sink. Such a cooling system 10 is known to those skilled in the art, for example a heat source in the form of an internal combustion engine and a heat sink in the form of a radiator.

Figure 2:
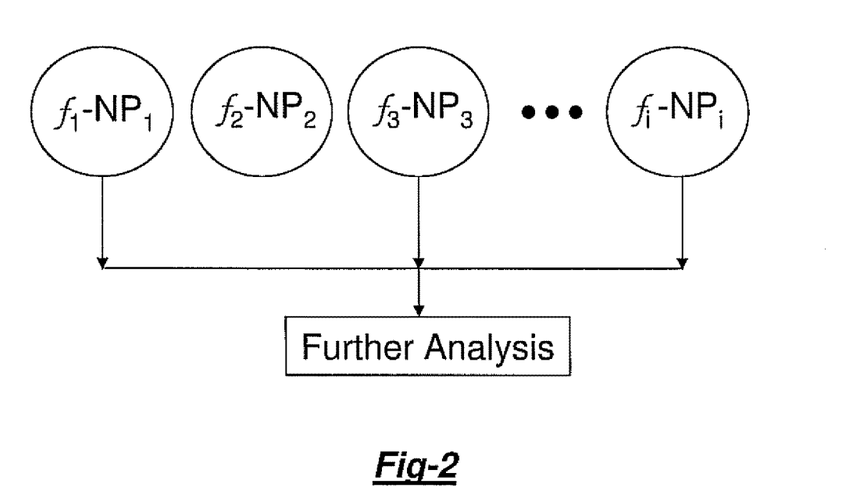
FIG. 2 is a schematic illustration of selecting a plurality of fluid-nanoparticle combinations for further analysis.
Figure 3:
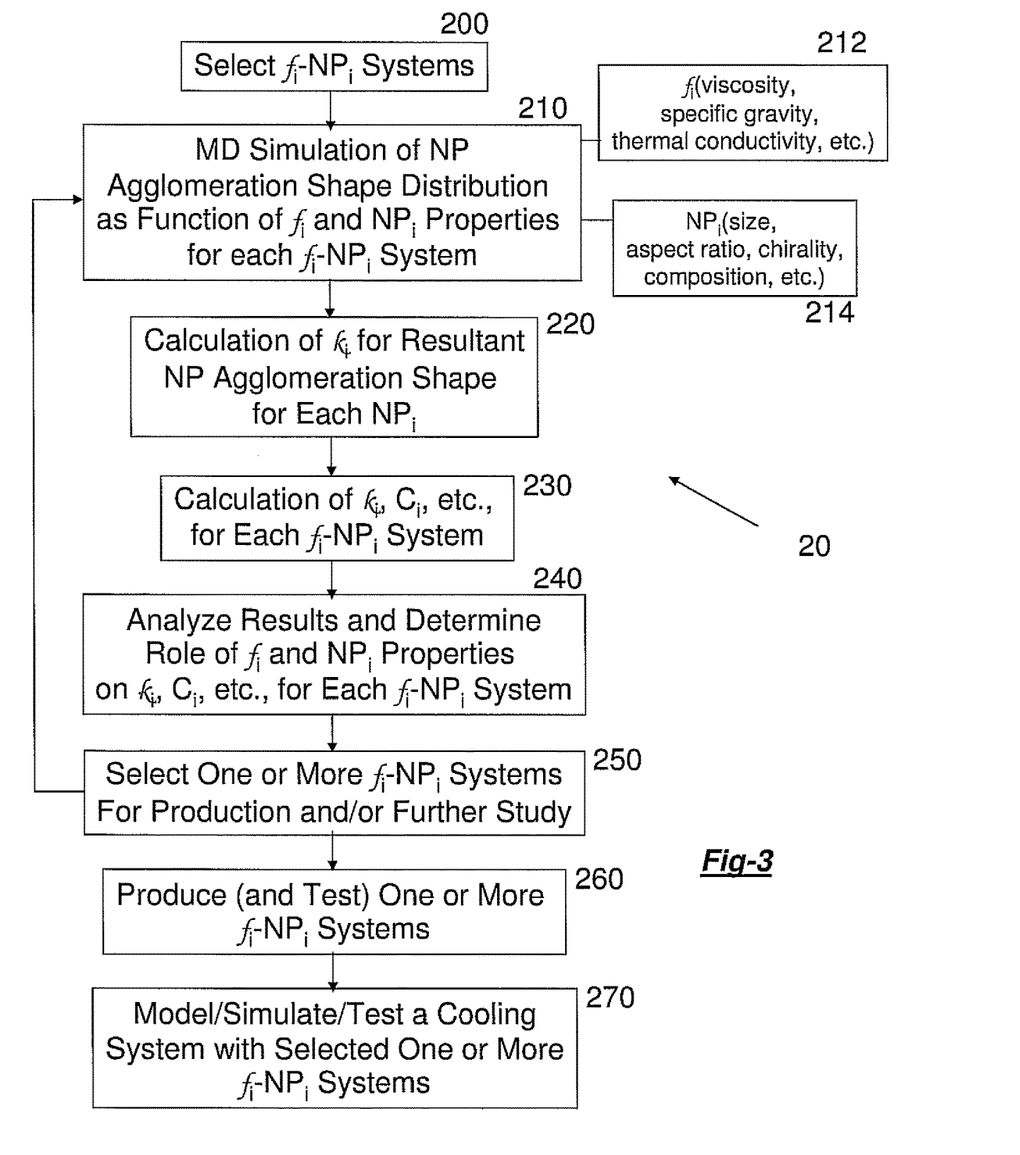
FIG. 3 is a schematic flowchart for a process according to an embodiment of the present invention.

Turning now to FIGS. 2 and 3, the process includes selecting a plurality of fluid-nanoparticle (f-NP) combinations for further analysis. For example and for illustrative purposes only, FIG. 2 illustrates a plurality of fluid-nanoparticle combinations, $f_1$-$NP_1$, $f_2$-$NP_2$, $f_3$-$NP_3$ . . . $f_i$-$NP_i$, from which a plurality of combinations can be selected. After the combinations have been selected as shown at step 200 of process 20 shown in FIG. 3, a molecular dynamic (MD) simulation of nanoparticle agglomeration shape distribution can be performed at step 210. The simulation can be a function of fluid and/or nanoparticle properties for each of the fluid-nanoparticle systems, for example and for illustrative purposes only, the viscosity, specific gravity, thermal conductivity, etc. of the fluid as shown at 212 and/or the size, aspect ratio, chirality, composition, etc. of the nanoparticles as shown at 214.

A calculation of the thermal conductivity ($k_i$) for resultant nanoparticle agglomeration shapes for each fluid-nanoparticle system can be calculated at step 220 and the calculation of a thermal conductivity, heat capacity, etc. for each of the fluid-nanoparticle systems can be calculated at step 230. At step 240, the results of the calculations from step 230 can be analyzed such that the role of the fluid and/or nanoparticle properties on the thermal properties for each of the fluid-nanoparticle systems can be determined. In addition, one or more of the fluid-nanoparticle systems can be selected for production and/or further study at step 250 while one or more of the fluid-nanoparticle systems selected at step 250 can be produced and/or tested at step 260. Based on testing conducted at step 260, modeling, simulation, and/or testing of a cooling system with a selected fluid-nanoparticle system can be performed at step 270. In this manner, first principles can be used to develop a cooling fluid, a cooling system, and the like. Stated differently, the use of molecular dynamics to calculate/determine the thermal conductivity, heat capacity, etc. of a particular fluid-nanoparticle coolant can be used to aid in the design of cooling fluids for a particular cooling system.

The fluid-nanoparticle combinations can include fluids such as water, alcohol, and the like. The nanoparticles can be nanotubes such as carbon nanotubes or, in the alternative, non-carbon nanotubes such as tungsten sulfide nanotubes, nickel chloride nanotubes, vanadium sulfide nanotubes, titanium sulfide nanotubes, and the like. In addition, it is appreciated that the nanoparticles can be a mixture of nanoparticles, for example nanotubes having different compositions, sizes, aspect ratios, chirality, and the like. Furthermore, with the molecular dynamic simulation of such systems, the need to produce actual fluid-nanoparticle solutions is greatly reduced and thus can provide a significant cost saving in the development and production of cooling fluid systems.

In order to better illustrate, but in no way limit the scope of, the invention, at least one example of a process according to an embodiment of the present invention is discussed below.

Example

Atomistic simulations based on molecular dynamics, which is a fundamental/first principles technique, were used to calculate the agglomeration behavior of nanostructures and thus gain insight into nanoscale phenomena within a fluid. In particular, an MD approach was used to investigate the propensity of agglomerate formation of carbon nanotubes within water. Various systems of carbon nanotubes and water were simulated using the GROMACS MD package (version 4.0) developed at the University of Groningen. In addition, the carbon nanotubes were modeled with an OPLS-aa[2] force field and a simple point charge (SPC/E) model was used for rigid water molecules. A cutoff distance of 1.5 nanometers for Van der Waals and coulombic forces was used. Larger cutoff distances were found to produce identical results. Long range electrostatic forces were simulated with a particle mesh Ewald (PME) model.

Figure 4:
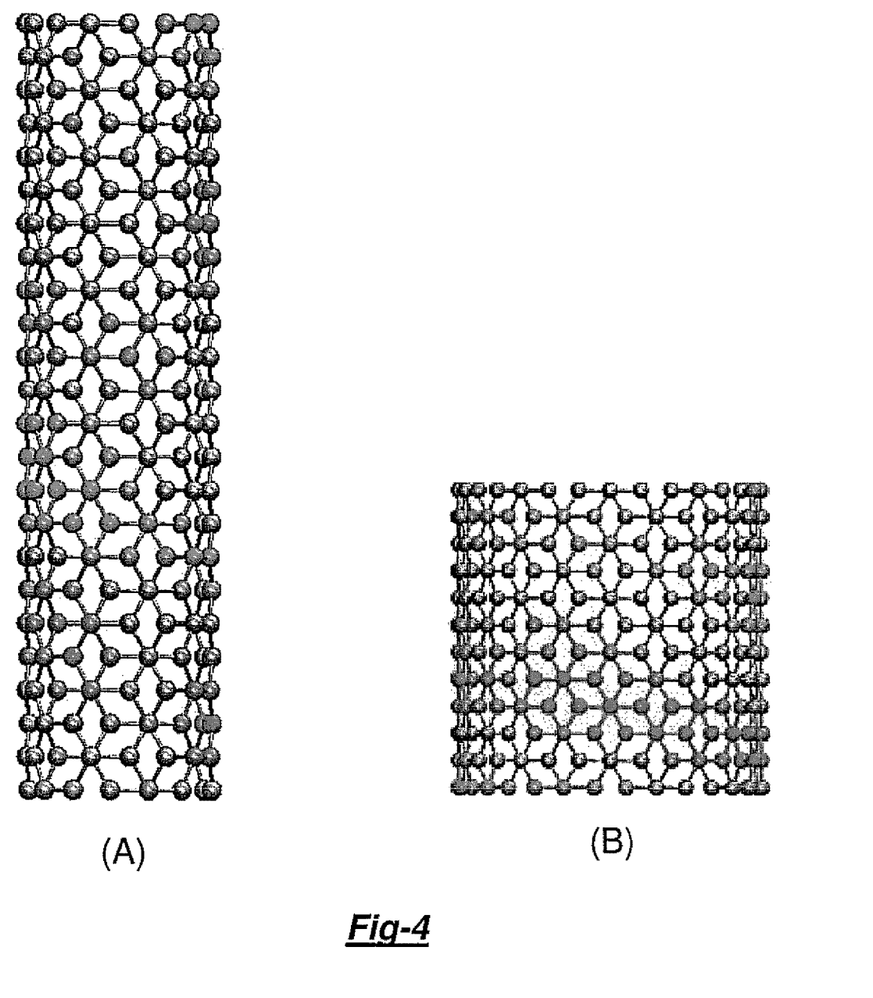
FIG. 4 is a schematic illustration of a nanotube having: (A) an aspect ratio of 4.0; and (B) an aspect ratio of 1.0.

In particular, sixteen carbon nanotubes were simulated in water for 10 nanoseconds at a fixed Mass fraction. Parameters that were varied in the simulations were:

Aspect ratio: An aspect ratio (AR) of 4.0 and 1.0 as illustrated in FIGS. 4A and 4B, respectively, was used. The carbon nanotubes having an AR of 4.0 had a diameter of approximately 0.7 nanometers while the nanotubes having an AR of 1.0 had a diameter of approximately 1.4 nanometers. The total number of carbon atoms in each nanotube was constant at 240 and four different systems having: (1) nanotubes with an AR of 4; (2) nanotubes having an AR of 1; (3) a mixture with equal numbers of nanotubes with an AR of 4 and an AR of 1; and (4) nanotubes having an AR of 20 were simulated.

Temperature of fluid. Temperatures of 280K, 315K, and 350K for each of the fluid-nanoparticle solutions were used.

Chirality. Chiralities corresponding to a zigzag structure (9,0), a chiral structure (7,3), and an armchair structure (5,5) or (10,10) were used in the simulations.

Figure 5:
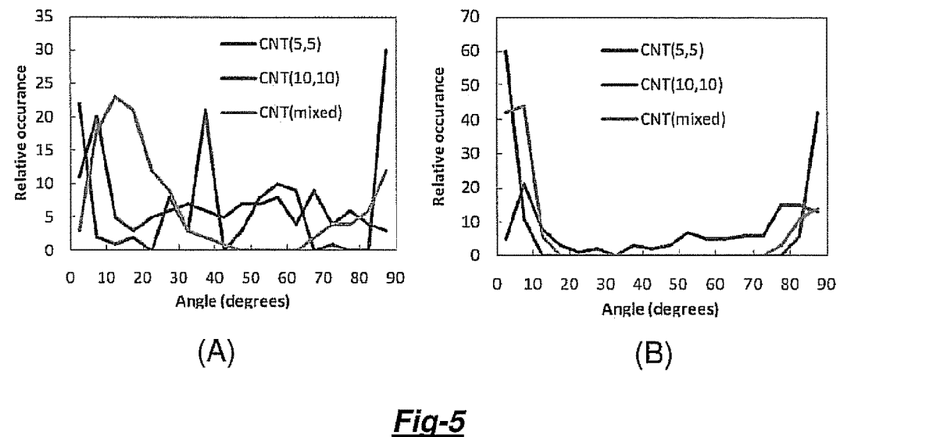
FIG. 5 is a graphical representation for the relative occurrence versus angle between adjacent nanotubes for different agglomeration shape distributions within water at: (A) 315K; and (B) 350K.

The angle between adjacent nanotubes was plotted as a function of relative occurrence for the nanotubes within the water solution as shown in FIG. 5. In particular, FIG. 5A illustrates the angle distribution for the three water-carbon nanotube systems at 315K and FIG. 5B illustrates the angle distribution for the same three systems at 350K. The distinct peaks for the water-nanotube system with nanotubes having an AR of 4.0 are seen in FIG. 5B while the system having nanotubes with an AR of 1.0 shows entirely different behavior. As such, the distribution as illustrated in FIG. 5B illustrates that a solution having nanotubes with a 1.0 AR has a less defined agglomeration shape distribution when compared to a combination having only nanotubes with an aspect ratio of 4.0. Although not as distinct, the same trend can be seen for the same systems with a water temperature of 315K (FIG. 5A). However, it is appreciated that the peaks for each of the systems are less well defined at the lower temperature and, as such, fewer agglomerates are formed at 315K compared to 350K.

Figure 6:
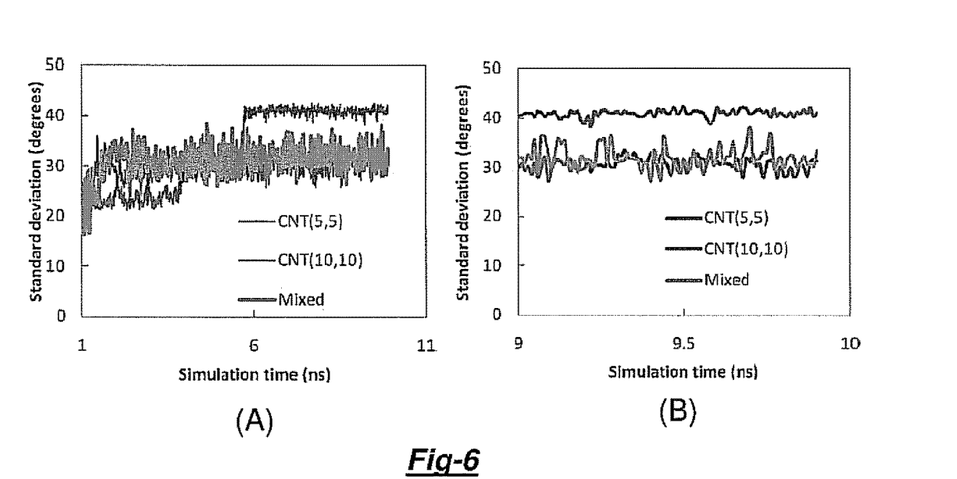
FIG. 6 is a graphical representation of the standard deviation of the angle between adjacent nanoparticles versus simulation time for the agglomerate shape distributions shown in FIG. 5.

The standard deviation of the angle distribution at each time step in the simulation was also calculated and is shown in FIG. 6. In particular, FIG. 6A shows the standard deviation for each system from 1 to 11 nanoseconds whereas FIG. 6B shows an expanded view for the same standard deviation between 9 and 10 nanoseconds. The deviations fluctuate around mean values towards the end of the simulation, thereby indicating a stable agglomerate configuration. However, FIG. 6A illustrates that the standard deviation changes significantly over the entire simulation; in particular, the angular deviation for the slender nanotubes shows a significant increase that corresponds to an agglomeration event.

Figure 7:
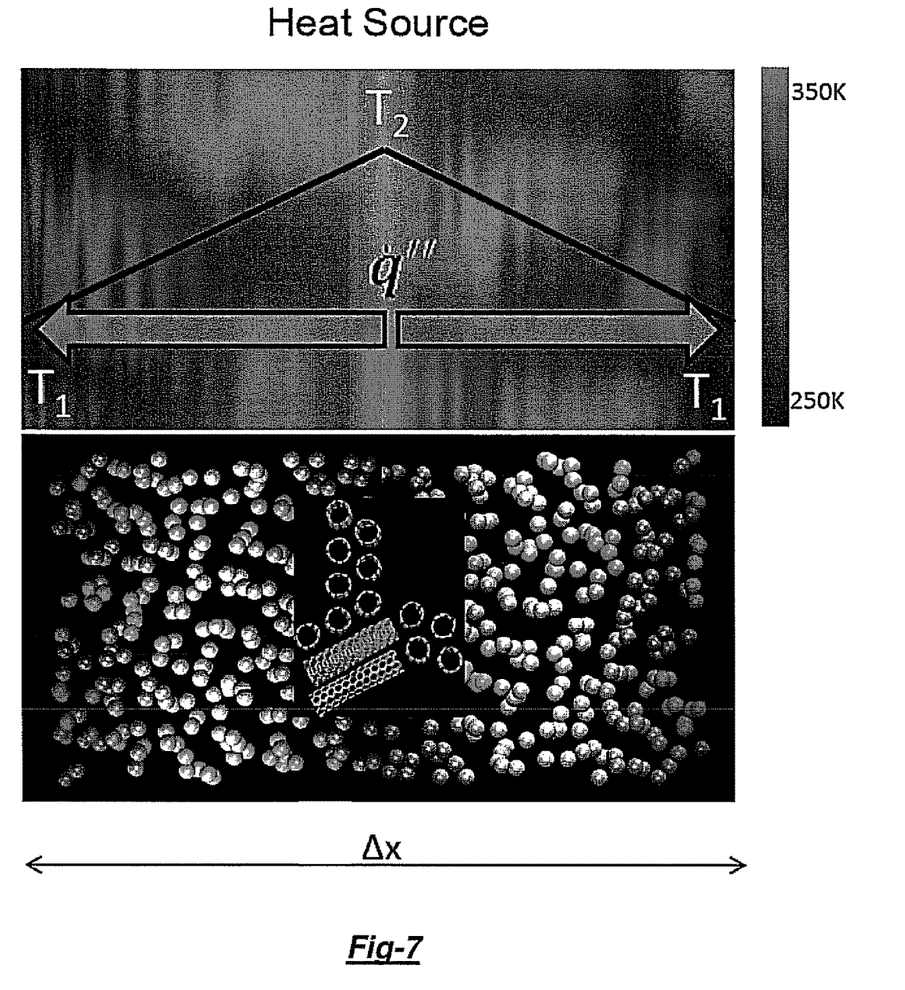
FIG. 7 is a schematic illustration for the flow of heat from a heat source using a molecular dynamics model.

Once the agglomeration shape distributions were calculated, evaluation of thermal conductivity for the nanotube agglomeration shapes was calculated. A non-equilibrium MD scheme developed by Muller-Plathe was used. Referring to FIG. 7, the method is illustrated for a monoatomic species such as argon. The method involves exchange of kinetic energies between individual atoms at the center and towards the sides of the domain ($\Delta x$). As such, atoms with the highest kinetic energy were chosen at the center of the domain/box and their kinetic energies were exchanged with atoms having lowest kinetic energy towards the end or outer sides of the box. Such an exchange resulted in a temperature gradient along the $\Delta x$ direction with the energy exchange at each relevant time step evaluated such that the heat flux was obtained using the correlation $$\dot{q}'' = \frac{\Delta E}{\Delta t A}$$

where A is the cross-sectional area of the domain in the direction normal to the chosen axis, and $\Delta t$ was the time duration of sampling. In addition, the temperature distribution at each time step was calculated which then afforded for the temperature gradient to be calculated therefrom. The thermal conductivity was then calculated using the relation $$k = \frac{\dot{q}''}{\Delta T / \Delta x}$$

where $\Delta T = T_2 - T_1$.

Figure 8:
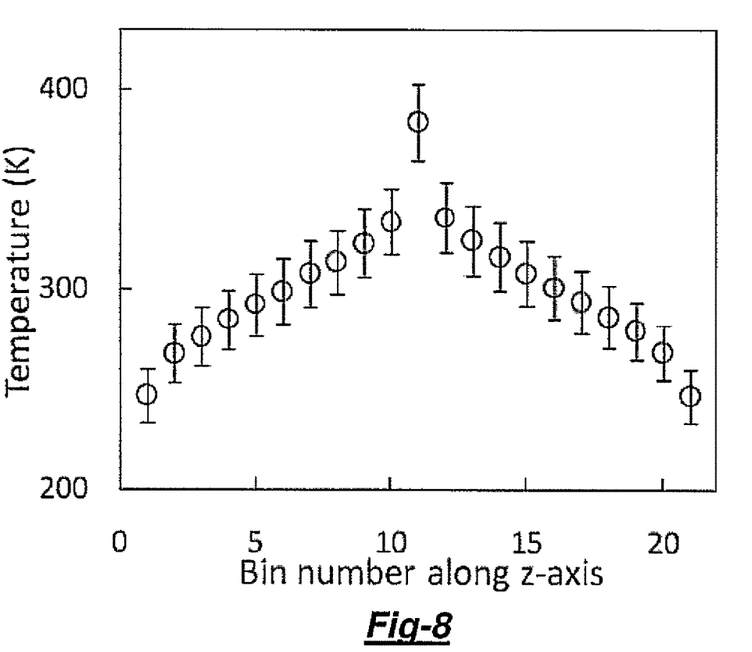
FIG. 8 is a calculated temperature profile related to the illustration shown in FIG. 7.
Figure 9:
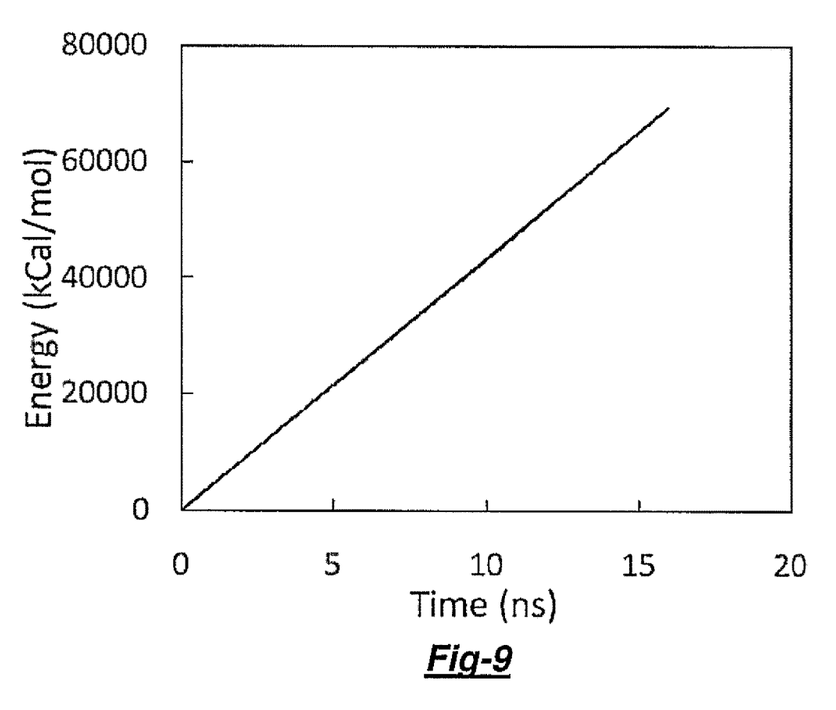
FIG. 9 is a graphical representation of energy exchanged from the heat source shown in FIG. 5 as a function of time.

For verification purposes, argon gas at 300K was simulated with a box having dimensions 42.45 nanometers×42.45 nanometers×84.9 nanometers containing 4096 atoms. The system was equilibrated for 1 nanosecond and a temperature gradient imposed by exchanging energy between two "hot" and "cold" atoms every 0.2 picoseconds. The corresponding heat flux and temperature gradients were calculated, from which the thermal conductivity was evaluated. In particular, the distribution of temperature at various points along a Z-axis was divided into 21 bins with the error bars for each temperature shown in FIG. 8. The distribution was symmetric and as expected consisted of a peak at the middle due to the exchange of kinetic energy at this location. A straight line was fit to the near-linear section of the distribution in FIG. 8 in order to obtain a temperature gradient. In addition, FIG. 9 illustrates a plot of the energy exchanged between the two hot and cold atoms with the energy rate obtained from the slope of this graph. It is appreciated that the energy flux was calculated by dividing this quantity by the cross-sectional area which then provided a thermal conductivity of argon as:

$$k = \frac{\dot{q}''}{\Delta T / \Delta x} = \frac{(69528.638 - 51847.651)}{63.44} \times (4.09 \times 10^{-5}) = 11.39 \times 10^{-3} \text{W}/mK$$

The experimentally determined value of thermal conductivity for argon gas at 300K is $16.0 \times 10^{-3}$ W/mK. While the calculated result is appreciated to have some deviation from the experimental value, it is reasonable as a first approximation.

For the large scale simulation of the fluid-nanoparticle systems, LAMMPS software was used to accept the output configuration obtained from the GROMACS MD package after being adapted to the LAMMPS format. Using the LAMMPS software, the overall thermal conductivity and heat capacity for the fluid-nanotube systems described above was calculated. Thereafter, one or more of the fluid-nanotube systems were selected for further study and/or production. In this manner, fluid-nanoparticle systems can be simulated with their agglomeration shape distribution, thermal conductivity, and the like calculated. Then based on the calculations, relevant factors and/or properties of the fluid and/or nanoparticles can be determined in order to produce a desired fluid-nanoparticle cooling fluid.

In addition to the above, it is appreciated that chemical and/or computational fluid dynamics can be used to model a cooling system having a cooling fluid with the properties calculated using molecular dynamics as described above. Furthermore, properties of the cooling fluid, such as settling of the nanoparticles, agglomeration behavior as a function of time, and the like can be simulated. In this manner, a particular fluid-nanoparticle system can be designed and/or used for a particular cooling system. For example and for illustrative purposes only, a fluid-nanoparticle solution that exhibits a relatively high thermal conductivity and/or heat capacity, but requires increased maintenance, more frequent replacement, etc. compared to a solution having a lower thermal conductivity and/or heat capacity but requires less maintenance, less frequent replacement, etc. can be designed and/or produced. As such, high performance engines subjected to relatively high levels of maintenance can have a "specialty" designed high performance cooling, whereas lower performance engines known to have a history of relatively low levels of maintenance can have a more "durable" but lesser performing cooling fluid designed therefor.

Furthermore, and as stated above, the process, method and/or systems disclosed herein can be used to execute or perform calculations for fluid-particle combinations, with results from such calculations extrapolated to one or more fluid-nanoparticle combinations. In addition, and in view of the teaching presented herein, it is to be understood that numerous modifications and variations of the present invention will be readily apparent to those of skill in the art. For example, other fluids than water and other nanoparticles than carbon nanotubes can be simulated for further study and/or production of cooling fluids. In addition, other software, methods, and the like can be used for the molecular dynamic simulations. As such, the foregoing is illustrative of specific embodiments of the invention, but is not meant to be a limitation upon the practice thereof. It is the following claims, including all equivalents, which define the scope of the invention.

We claim:

1. A process for designing and producing a cooling fluid for use in a cooling system, the process comprising:
    selecting a plurality of liquid-nanoparticle combinations to be simulated, each of the liquid-nanoparticle combinations including a liquid and a plurality of nanoparticles;
    calculating a nanoparticle agglomerate shape distribution for each of the liquid-nanoparticle combinations;
    calculating a thermal conductivity for each of the liquid-nanoparticle combinations as a function of the liquid, the plurality of nanoparticles and the nanoparticle agglomerate shape distribution for each of the liquid-nanoparticle combinations;
    selecting a liquid-nanoparticle combination as a function of the calculated thermal conductivities for the liquid-nanoparticle combinations;
    providing a liquid and a plurality of nanoparticles corresponding to the selected liquid-nanoparticle combination; and
    mixing the provided liquid and plurality of nanoparticles to produce a cooling fluid for use in a cooling system.

2. The process of claim 1, further including calculating a clustering behavior of the plurality of nanoparticles within the liquid for each of the liquid-nanoparticle combinations.

3. The process of claim 1, wherein the plurality of nanoparticles is a plurality of nanotubes and the plurality of liquid-nanoparticle combinations is a plurality of liquid-nanotube combinations.

4. The process of claim 3, wherein the calculated agglomerate shape distribution is a function of at least one liquid-nanotube combination property selected from the group consisting of a temperature of the liquid, an aspect ratio of the nanotubes, a length of the nanotubes, a chirality of the nanotubes, a homo-molecular nanotube system, a hetero-molecular nanotube system and combinations thereof.

5. The process of claim 4, wherein the agglomerate shape distribution is calculated using molecular dynamics.

6. The process of claim 5, wherein the thermal conductivity is calculated using a large-scale molecular dynamics simulator.

7. The process of claim 6, wherein the calculated thermal conductivity is a function of at least one liquid-nanotube combination property selected from the group consisting of a temperature of the liquid, an aspect ratio of the nanotubes, a length of the nanotubes, a chirality of the nanotubes, a homo-molecular nanotube system, a hetero-molecular nanotube system, a concentration of the nanotubes within the liquid, an agglomerate structure of the nanotubes within the liquid and combinations thereof.

* * * * *

UNITED STATES PATENT AND TRADEMARK OFFICE
CERTIFICATE OF CORRECTION

PATENT NO. : 10,468,124 B2
APPLICATION NO. : 13/355651
DATED : November 5, 2019
INVENTOR(S) : Tenghua Tom Shieh et al.

Page 1 of 1

It is certified that error appears in the above-identified patent and that said Letters Patent is hereby corrected as shown below:

On the Title Page

In item (56), references cited, US Patent Documents, US20060259285 A1, delete "Babel et al." and insert --Bahel et al.--, therefor.

In the Specification

In Column 4, Line 51, delete "Mass" and insert --mass--, therefor.

Signed and Sealed this
Sixteenth Day of June, 2020

Andrei Iancu
*Director of the United States Patent and Trademark Office*